United States Patent [19]

Joncour

[11] Patent Number: 4,653,881
[45] Date of Patent: Mar. 31, 1987

[54] APPARATUS FOR MEASURING THE PARAMETERS REQUIRED WHEN MOUNTING OPHTHALMIC LENSES UPON A SPECTACLES FRAME

[75] Inventor: Christian Joncour, Paris, France

[73] Assignee: Essilor International (Compagnie Generale d'Optique), Creteil, France

[21] Appl. No.: 694,685

[22] Filed: Jan. 25, 1985

[30] Foreign Application Priority Data

Jan. 31, 1984 [FR] France ................. 84 01451
Jan. 7, 1985 [FR] France ................. 85 00137

[51] Int. Cl.$^4$ ................................. A61B 3/10
[52] U.S. Cl. ........................ 351/204; 33/200
[58] Field of Search ............ 351/204, 211; 33/200

Primary Examiner—Rodney B. Bovernick
Attorney, Agent, or Firm—Burgess, Ryan & Wayne

[57] ABSTRACT

Device for measuring the ocular parameters of a patient, especially parameters for mounting ophthalmic lenses on a spectacle frame with a view to their adaptation to the patient, wherein a reference mark assembly includes two pairs of height reference marks respectively associated to the two eyes of the patient, and distance reference marks each associated to a lateral mirror so as to receive the profile image of the eye of the patient and of the lens and its associated rim and wherein the device further includes a measuring device to evaluate the position of the different above-mentioned reference marks with respect to the patient's eyes, to the lens and associated rim, and to visualize the results of this evaluation.

12 Claims, 11 Drawing Figures

APPARATUS FOR MEASURING THE PARAMETERS REQUIRED WHEN MOUNTING OPHTHALMIC LENSES UPON A SPECTACLES FRAME

FIELD OF THE INVENTION

The present invention concerns an apparatus for measuring the parameters required when mounting ophthalmic lenses upon a spectacle frame.

The optician responsible for correctly adjusting upon a selected spectacle frame the ophthalmic lenses previously prescribed by a specialist must determine with accuracy certain mounting parameters in order that the lenses, once fixed in position, may fulfill their corrective purpose under optical conditions of lens positioning with respect to the respective eye of the patient upon which conditions ophthalmologists depend in order to establish their prescription. These parameters are determined in particular, on the one hand, by the spacing between the patient's pupils and/or their "half-spacing", i.e. the distance between the pupil involved and the vertical median plane of the nose and, on the other hand, by the distance between each pupil and the lower edge of the respective ophthalmic lens, which indicates the mounting height of the lens, and furthermore by the distance between the lens and the cornea of the respective eye.

BACKGROUND OF THE INVENTION

Apparatus allowing the optician to determine these parameters already exist and generally comprise a housing defining, on the one hand, at one of its ends, a target aperture intended to receive the spectacles worn by the patient and his corresponding facial portion, as well as, on the other hand, at the opposite end, an ocular aperture provided with an eye-piece aligned on the target aperture and intended to allow the optician to observe the ophthalmic lenses and the patient's eyes while, in the housing, a lens is placed between the two apertures, the optical axis of which coincides with that of the eye-piece, and a light source disposed outside the optical axis of the said lens is disposed so as to emit a luminous beam towards the said lens and the target aperture, in the direction of the said optical axis, optical reflecting means allowing the optician to receive through the said eye-piece frontal and lateral images of the ophthalmic lenses superimposed upon the patient's eyes, as well as optical marking and measuring means are interposed on the path of the luminous rays between the target aperture and the eye-piece in such a manner that their images are visible to the optician at the same time as the above-mentioned images.

An apparatus of this type is in particular disclosed in German Pat. No. 1 060 622. This known device utilizes as optical reflecting means, for each of the patient's eyes, two prisms that send back the lateral image (i.e. the image of the profile) of the cornea, associated to the image of an adjusting mark provided on one of the prisms, towards the ocular aperture where it is superimposed on the frontal image of the cornea—thus of the pupil—that is transmitted towards the ocular aperture without optical reflection, but with the interposition, on the optical path, of reference marks, such as lines or cross-hairlines. This arrangement is supposed to allow the optician, through the lateral images of the two corneas and the associated reference marks to prevent any angular shift of the device in the horizontal plane, with reference to the correct symmetrical position with respect to the patient, in which the image of each of the said adjusting marks must be at a tangent to the apex of the cornea involved.

The known device is not designed for the appreciation, by the optician, of the distance separating the spectacle lenses from the corresponding pupils of the patient, nor for measuring the "mounting height" of the lenses, i.e. the distance between each pupil and the lower edge of the associated lens. Without doubt it allows measurement of the distance between the pupils, or their "half-distance" avoiding measuring errors due to an angular shift of the device with respect to the eyes of the patient, but this result—which in itself is already limited—requires a relatively complex handling on the part of the optician, who is in fact limited by the basic conception of the device, to adjust it in depth with respect to the patient, which constitutes a time-consuming operation. Furthermore, in the disposition of a device such as that disclosed in the above-mentioned German patent, the optical path of the lateral images of the corneas passes through the central zone of the lens and is deflected prior to reaching this zone. Due to this fact, the lens must be placed at a relatively great distance from the patient's eyes, which comprises a risk of parallax is errors resulting in turn, in measuring errors. Another drawbacks of the known device lies in the fact that due to the "cranked" plotting of the optical path of the lateral images of the corneas, in front of the lens, these images are at the level of the ocular aperture, therefore, for the optician, shifted in depth with respect to the frontal images of the corneas and the pupils. This comprises for the optician the necessity of accomodating in order to see at the same time the two images in a clear manner. Then it is well known that such an accomodation induces a substantial and undesirable fatigue.

In another device, disclosed in French Pat. No. 1 506 352, the optician sees through the lens the image of the patient's eyes, and by displacing the reference marks in order to cause them to coincide with the reflection supplied by the corneas or "corneal reflection", he can measure the pupillar "half-spacing" of the patient. Using another set of reference marks, arranged perpendicularly to the first, the optician can set a reference line in a tangent position with respect to the lower edge of the spectacles lens or its rim or eye-wire and consequently determine the "mounting height". He can, furthermore, also measure the distance between the patient's eye and the associated spectacles lens, by placing the device laterally with respect to the associated spectacles frame.

While allowing to measure all the required lens mounting parameters, this prior device involves for the optician a plurality of steps in handling said device, as well as an ascertained habit of measuring there with, since this device has to be displaced and replaced several times with respect to the spectacle-wearing patient.

The aim of the present invention is to provide a device of the type defined herein-above that does not present the drawbacks of the known devices, which allows to measure all the parameters required for mounting lenses on spectacle frames by simple operations, without complicated handling of the device, which reduces to a minimum the visual accomodation required by the optician and supplies accurate measuring results, free of parallax is or other errors and the dimension and cost of which are reduced.

With this purpose in view, the invention provides an apparatus for measuring the ocular parameters of a patient, especially the parameters required for mounting ophthalmic lenses on a spectacle frame with a view to adaptating the same to the needs of the patient, comprising a housing defining, at one of its ends, a target aperture intended to receive the rims or eye wires and lenses of the spectacle worn by the patient, and at the opposite end, an ocular aperture aligned with said target aperture and provided with an eye-piece intented to be observed by an operator, the said housing containing a light source adapted to emit a luminous beam towards the said target aperture, a bi-convex lens or a Fresnel lens interposed between the said target aperture and the eye-piece so that its optical axis coincides with that of the eye-piece and so that the said lens forms for the operator, in association with the eye-piece, frontal and lateral images of the lenses and lens-rims of the spectacle frame, as well as the eyes of the patient, reference marking means that are adapted to be adjusted with respect to the patient's eyes and the image of which is intended to be observed through the said eye-piece, simultaneously with the said frontal and lateral images, wherein the said reference marking means comprise two pupil spacing reference marks each disposed on a transparent portion of a spacing reference mark holder displaceable independently from the other horizontally and perpendicularly to the above-mentioned optical axis, through a manually actuated control mechanism by using a spacing adjustment member accessible from the outside of the housing, the said reference marking means furthermore comprising two pairs of height reference marks associated respectively to the two eyes of the patient, each height reference mark being disposed on a transparent portion of a vertical height reference mark holder displaceable independently from the others, the said reference marking means comprising furthermore two distance reference marks each associated to a lateral mirror placed laterally with respect to the patient's eye, in a vertical plane inclined substantially at 45° with respect to the optical axis in such a way as to receive the profile image of this eye, of the ophthalmic lens and of the associated spectacle rim and to send it back to a first deflecting mirror placed in a vertical plane perpendicular to that of the lateral mirror and transmitting said profile image toward the optical axis to a second deflecting mirror placed adjacent to said axis in a vertical plane substantially inclined at 45° with respect to that of the first deflecting mirror, in such a way as to transmit said profile image towards the eye-piece, and wherein the said device comprises measuring means for evaluating the position of said reference marks with respect to the eyes of the patient, to the said ophthalmic lenses and to the said spectacle frame, and for visualizing the results of this evaluation.

In one embodiment, the control mechanism of each of the two pupil spacing reference mark holders comprises a rectilinear rack extending transversally to the optical axis and meshing with a pinion integral with a spacing adjustment knob and coaxial to it, the said knob being mounted for rotation about a vertical axis orthogonal to the optical axis, and partially projecting from that wall of the housing which is located opposite in the target aperture, said rack being integral with one of the ends of a cranked rod that bears on its other end the associated spacing marking holder.

According to one advantageous feature of this device the control mechanism of each of the four height reference marking holders comprises a control rod mounted through hinge means, at a location between its two ends, on a vertical and longitudinal wall of the housing, so as to be displaceable in a vertical plane parallel to said optical axis, and bearing at one of its ends, the corresponding height reference mark holders, while the said hinge means comprise a guiding stud laterally disposed on the control rod and slidably engaging in a curved guiding channel or groove provided in the said internal wall, and a curved rack meshing with a pinion integral with a height adjustment knob and coaxial to it, the arrangement being such that each reference mark holder is displaced, along a substantially rectilinear vertical path.

According to another feature of the device, the two pupil spacing reference mark are associated to a spacing scale allowing to measure the horizontal distance between these reference marks and the horizontal distance between the vertical median nasal plane of the patient and each of the said spacing reference marks, the said spacing scale being disposed in a fixed transparent plate mounted in the housing between the target aperture and the spacing and height reference mark holders, where each pair of height reference mark holders is associated to a height scale allowing to measure the vertical distance between the two respective reference mark holders of each pair thereof, the said height scale being disposed on a portion of the lower height reference mark holder of each pair which covers at least partially the associated upper height reference mark holder, while the distance reference marks are each associated to a distance scale disposed on the associated lateral mirror and allowing to measure, in the image received by the eye-piece, the distance between the patient's cornea and the associated distance reference mark.

In a particularly advantageous embodiment, the control mechanisms of the pupil spacing reference mark holders and the height reference mark holders are associated to electric and electronic means adapted to detect the distances between matching reference marks, to produce electric signals representating these distances, to transform these electric signals into digital signals and to use them to display in digital form the said distances by using display windows disposed on the walls of the housing.

Preferably, the two adjustment knobs of the control mechanisms of each pair of height reference mark holders are kinetically connected respectively to the slider and to the resistor of a rotary potentiometer the terminals of which are connected to at least one input terminal of the electronic means of which at least one output terminal is connected to one of said windows for displaying the effective resistance of the potentiometer determined by the relative angular position of the two above-mentioned knobs and representing the vertical distance between the two height reference marks concerned.

According to another advantageous aspect of the present invention, each spacing adjustment knob is kinetically connected to the slider of a potentiometer the terminals of which are connected to the input terminals of the said electronic means of which at least one output terminal is connected to at least one of the said windows for digitally displaying the value of the effective resistance of the potentiometer determined by the angular position of the adjustment knob concerned.

In a preferred embodiment, the said light source is a light source constituted by four punctual diodes disposed at the four corners of a square so as to not to be visible directly by the eye of the operator, the centre of the square being on the optical axis of the eye-piece.

In another embodiment, the above-mentioned lateral mirrors are semi-transparent mirrors that are each provided with an adjustment mark and behind each of which is disposed a plate provided with a distance scale, so that the said eye-piece receives, for each of the patient's eyes, simultaneously the profile image of the eye, the profile image of the eye-wire concerned, the image of the reference mark line and the image of the said distance scale.

In this embodiment, at least one of the semi-transparent lateral mirrors is advantageously pivotally mounted around an orthogonal axis of the said optical axis, so that in the image received in the eye-piece the suitably oriented reference mark of this semi-transparent lateral mirror can be brought through pivoting to be substantially superimposed upon the profile of the rim, while the angle of this pivoting represents the inclination of the said rim.

In a variant, the light source is shifted with respect to the said optical axis and the light beam is sent towards the target aperture through a semi-transparent mirror inclined with respect to this axis and interposed on it between the said target aperture and the said eyepiece, towards which it allows to pass the reflected images of the spectacles and the eyes of the patient, as well as the images of the concerned reference means.

BRIEF DESCRIPTION OF THE DRAWINGS

The invention will be described herein-below in further detail, especially with reference to the appended figures which show, by way of non-limitative illustration, several embodiments of the invention.

Figure 1:
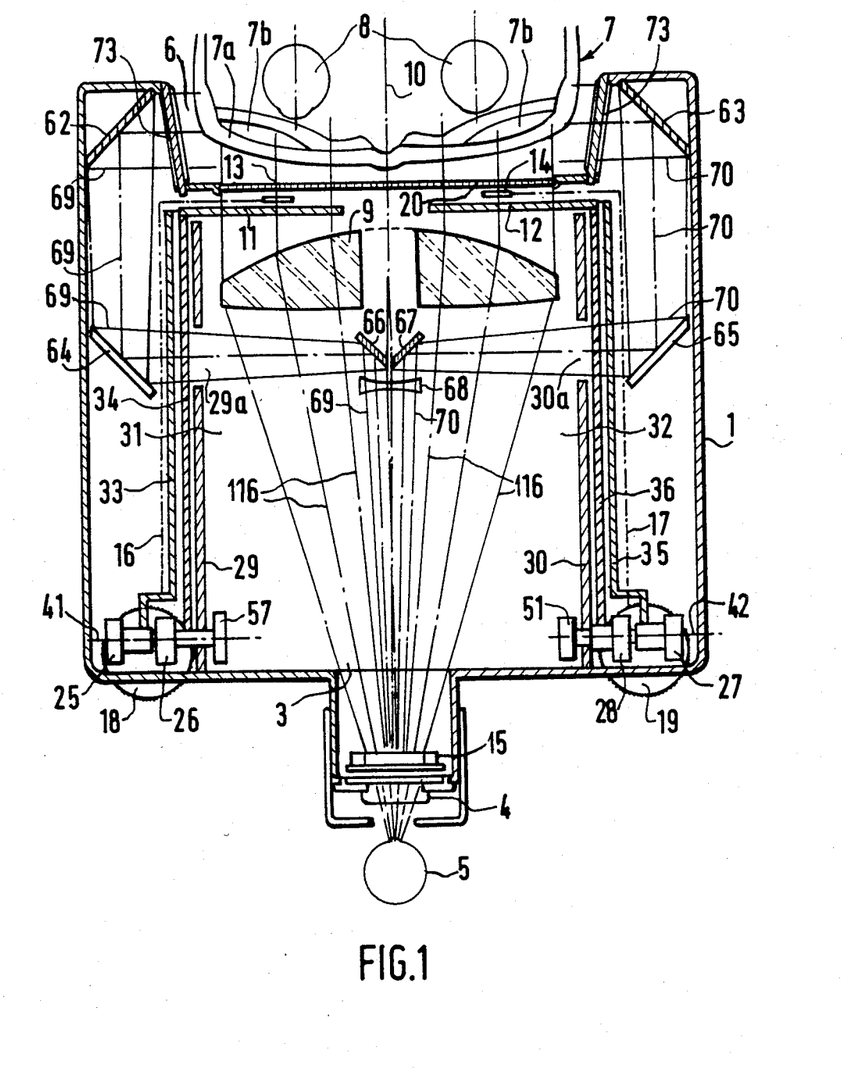
FIG. 1 shows a horizontal section of an embodiment of the of the measuring device according to the present invention.
Figure 2:
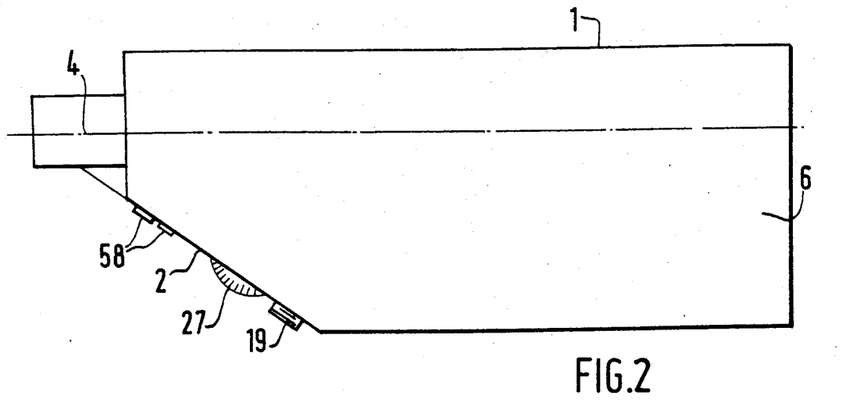
FIG. 2 shows the device in lateral elevation.

The device such as represented, especially in FIGS. 1 and 2, comprises a housing 1 having an overall rectilinear form presenting, from the side view (FIG. 2) at one of its ends, an inclined end wall part 2. At this same end, the housing is provided with an ocular aperture 3 in front of which is disposed an eye-piece 4 adapted to allow the optician or similar practitioner, whose eye is indicated as reference 5 in FIG. 1, to proceed with the observation and measurement operations required. At the end opposite eye-piece 4, housing 1 defines an aperture 6 called "target" which is adapted to receive the front portion of spectacles 7 to be examined, worn by the patient whose eyes are indicated as reference 8 (FIG. 1).

A lens 9, preferably bi-convex, is disposed in fixed position between apertures 3 and 6 so that its optical axis 10 coincides with that of eye-piece 4 and with the common median axis of apertures 3 and 6. Between lens 9 and target aperture 6 are disposed two pairs of transparent height reference mark holders 11 and 12 substantially vertically displaceable (i.e. in a plane perpendicular to that of FIG. 1), in reference to the normal service position of the device, with this purpose, in a manner and by means described herein-below. Each of pairs 11, 12 comprise two vertically superimposed reference mark holders, that are displaceable independently from each other. Between target opening 6 and height reference mark holder 11, 12 and immediately adjacent to it, are interposed two transparent spacing reference holders 13 and 14 horizontally displaceable independently of each other for purposes and means described hereunder. Therefore, as can be seen from FIG. 1, the pair of height reference mark holders 11 and the spacing reference holder 13 are associated to one of the eyes 8 of the patient while the other pair of height reference mark holders 12 as well as the other reference mark holder 14 are associated to the other eye. Lenses 7b of spectacles 7 worn by the patient are interposed, in service position of the device, between the eyes 8 of the patient and spacing mark holders 13, 14.

Eye-piece 4 is associated to an annular or peripherical light source 15 disposed, in a manner known per se, so as to be invisible to eye 5 of the optician while emitting a luminous beam in the direction of target aperture 6, through lens 9 and reference mark holders 11, 12, 13 and 14. The luminous rays are reflected at the level of the cornea, thus substantially at the pupil, of each eye 8 and returned to eye-piece 4 and eye 5 of the optician, along a path 116 determined by lens 9 that they pass through again. The optician therefore sees the image of the pupils of the patient and, by superimposition, the image of the reference marks disposed respectively on each spacing reference mark holder 13, 14 and each of the height reference mark holders forming pairs 11 and 12, and by using means that are further described hereafter, he proceeds to the adjustment of the said reference marks with respect to the patient's pupils in order to thereafter read off the above-mentioned spacing and height parameters of the pupils.

Light source 15 is preferably constituted by four paint diodes disposed at the four corners of a square, the centre of the square being situated on the axis of eye-piece 4.

Figure 7:
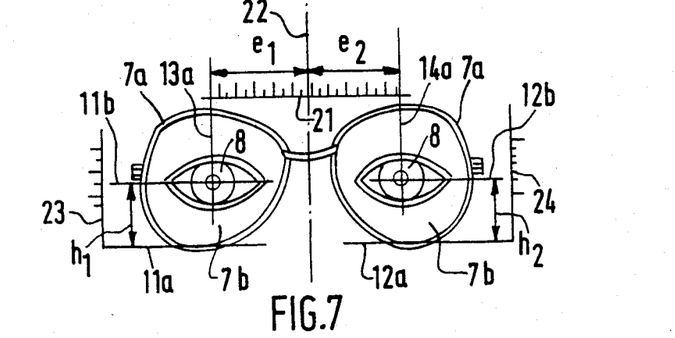
FIGS. 7 and 8 represent schematically the different parameters measured by means of the device according to the invention.

Each of spacing reference mark holders 13, 14 is constituted by a transparent plate or plaquette provided with a thin vertical reference line, which on the outline of FIG. 7 is indicated, as 13a for reference mark holder 13 and as 14a for reference mark holder 14.

Reference mark holders 13, 14 are each horizontally displaced in a plane perpendicular to optical axis 10 by means of a mechanism, indicated diagrammatically by mixed lines 16 and 17, respectively, that are controlled by a knob 18, 19 rotatably mounted in a horizontal plane around an axis orthogonal to optical axis 10. Knobs 18, 19 preferably knurled, project towards the outside of inclined wall 2 of housing 1, as shown in particular in FIG. 2. Mechanisms 16, 17 are of any suitable type, known per se, for example of the rack and pinion type or an endless screw or worm that allows to horizontally displace, in two opposite directions, associated reference mark holder 13 or 14 in response to a rotation, in either direction, of corresponding control knob 18 or 19.

Figures 3, 5:
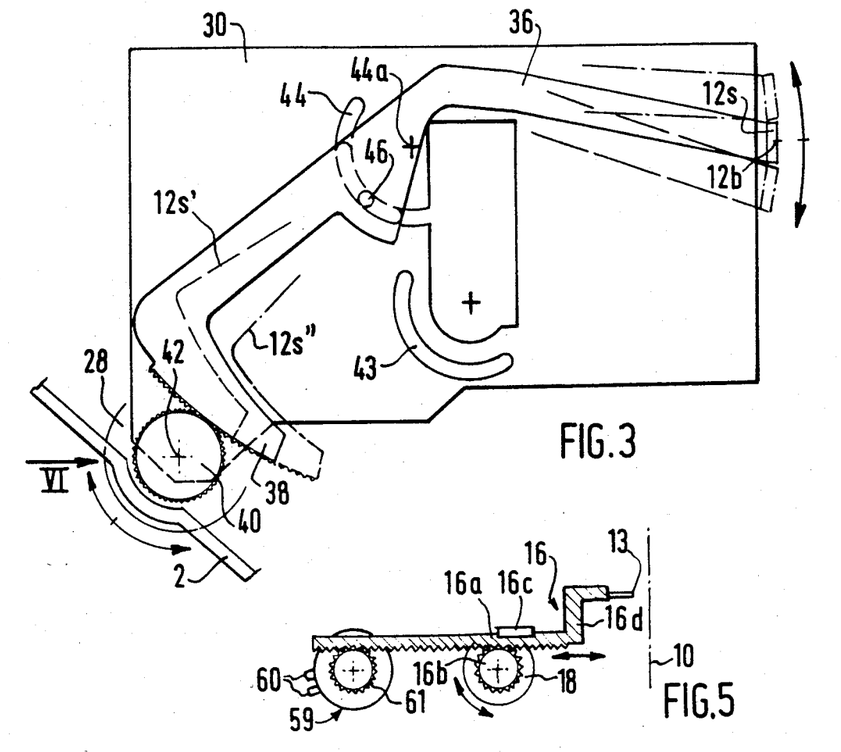
FIG. 3 diagrammatically represents in lateral elevation, the adjustment mechanism of an upper reference mark utilized for measuring the distance between a pupil and the lower edge of the associated spectacle lens.
FIG. 5 shows schematically, in a plane view, one of the mechanisms controlling the horizontal displacements of the reference marks which are used to measure the spacing between the pupils.

One example of control mechanism 16 able to fulfill this function is represented in a highly diagrammatized manner in FIG. 5, where the said mechanism comprises a pinion 16b integral with the rotating control knob 18 and meshing with a rack 16a suitably guided in 16c, for example at the bottom of housing 1, in such a way as to be horizontally displaceable in a direction perpendicular to optical axis 10; rack 16a is connected by a cranked wire or rod 16d to reference mark holder 13 which is thus integrally displaceable with the rack and, due to this fact, horizontally adjustable with respect to the pupil of the associated eye 8. It is understood that mechanism 17 associated to reference mark holder 14 and control knob 19 and arranged in the same way is symmetrically disposed with respect to mechanism 16.

Figure 10:
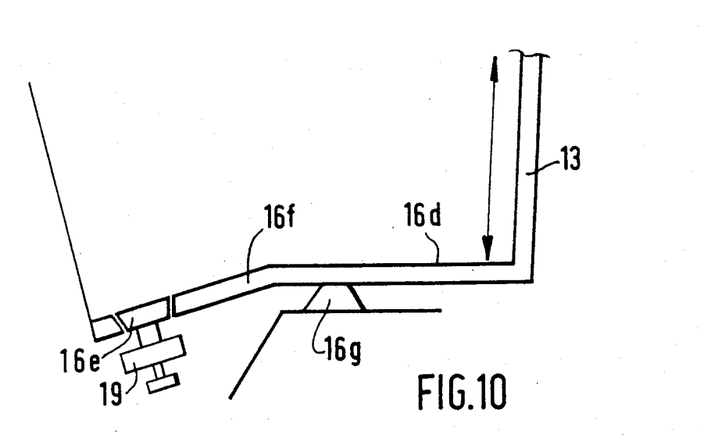
FIG. 10 is, in cross-section, a variant of the mechanism described in FIG. 5.

Another example of this kind of mechanism is represented in FIG. 10. On the mechanism thus represented, control knob 18 to which is associated the potentiometer, controls the rotation of a conical pinion 16e meshing with a circular rack 16f rotatably borne by an axle or spindle 16g. Rack 16f is connected by the cranked wire or rod 16d to reference mark holder 13 to which it is associated and which is thus angularly displaceable.

A suitably graduated spacing scale, referenced 21 in the outline of FIG. 7, can be engraved, for example on a fixed transparent plaquette 20 disposed in housing 1 between eyes 8 of the patient and reference mark holders 13, 14. The optician, whose eye 5 perceives the superimposed images of each pupil of the patient, the reference mark lines 13a, 14a and the graduated horizontal scale 21 can thus cause to coincide by acting upon control knobs 18, 19 each reference mark line 13a, 14a of reference mark holders 13, 14 with the vertical axis of the pupil of associated eye 8 and thus read off visually on graduated scale 21 the total spacing between the pupils and/or their "half-spacings" with respect to the median nasal plane 22 of the patient, referenced 22 in the outline of FIG. 7 which also shows said pupillary half spacings $e_1$ and $e_2$ of which the total $e_1+e_2$ represents the total pupillary spacing.

Furthermore, each reference mark holder 12i, 12s (FIGS. 3 and 4) of the vertically superimposed pair of reference mark holders 12 comprises a transparent plaquette provided with a horizontal reference mark line. The outline of FIG. 7 shows as reference 12b the line or mark of the upper reference mark holder 12s of pair 12, and as 12a the line or mark of the lower reference mark holder 12i of this pair. A vertical graduated scale 24 (FIG. 7) can be provided, for example, on a transparent element integrally displaceable with lower reference mark holder 12i, such as an extension 12p of reference mark holder 12i, which is horizontally superimposed on upper reference mark holder 12s, allows the optician to visually measure the height of upper reference mark 12b with respect to lower reference mark 12a.

Lower reference mark holder 12i is supported at the far end of a cranked control wire or rod 35 the nearer end of which is provided with a concave rack 37 meshing with a straight pinion 39 integral with a rotary control knob 27 and coaxial to it. Knob 27 turns around a horizontal geometric axis 42 (FIGS. 1, 3 and 4) orthogonal to optical axis 10. This knob extends from the inclined wall 2 towards the outside (FIG. 2). In a hinged zone 32 (FIG. 1), internal wall 30 is provided with a guiding groove or channel 43 in the form of an arc of a circle around a centre 43a. Control rod 35 bears a guiding pin or stud 45 engaged in groove or channel 43. It will be understood that, due to this arrangement, it is possible by turning button 27, to displace, in a vertical plane and according to a composite shifting movement, control rod 35 in order to cause to raise or lower its far end, thus reference mark holder 12i, so that this latter follows a path which, however slightly concave, is assimilable to a substantially rectilinear path.

It is, of course, possible to take into account the errors due to the slightly concave path of reference marks 11a, 11b, 12a, 12b by including in the display programme of electronic device EL, that will briefly be described herein-below, a correction programme taking into account the concave ray trace of the marks.

Figures 4, 6:
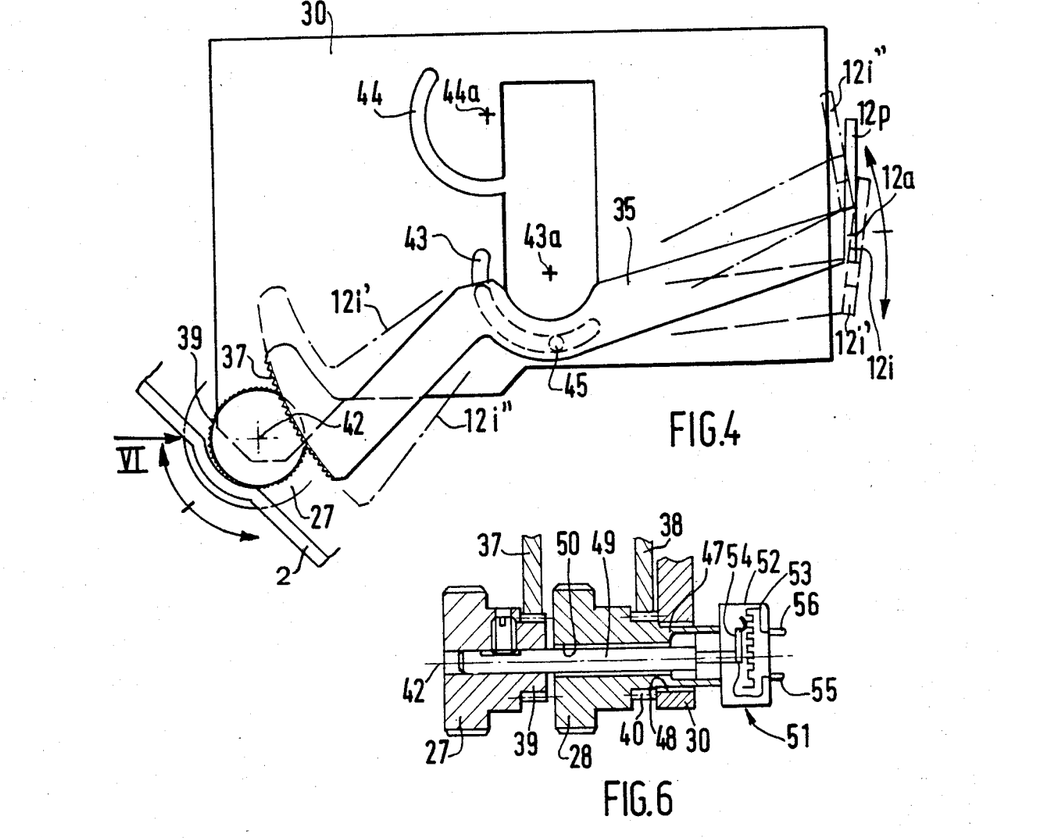
FIG. 4 is a view similar to that of FIG. 3, but which shows the adjustment mechanism of the corresponding lower reference mark.
FIG. 6 shows schematically, in cross-section along the direction indicated by arrow VI in FIGS. 3 and 5, the disposition of the control knobs of mechanisms of FIGS. 3 and 4, as well as the associated potentiometer.

Upper reference mark holder 12s associated to lower reference mark holder 12i of the pair 12 is controlled by a mechanism in every way identical to that which has been described immediately herein-above. Indeed, this reference mark holder 12s is mounted on the far end of a cranked control rod 36 displaceable in a vertical plane parallel to optical axis 10, around a hinge arranged like that of rod 35, with respect to internal wall 30. A guiding groove or channel 44 in the form of an arc of a circle with centre 44a, provided in internal wall 30 above curved groove or channel 43 and slightly shifted horizontally with respect to it, receives a guiding cap 46 integral with rod 36, while a curved rack 38 meshes with a straight pinion 40 integral with a rotating control knob 28 and coaxial to it. Axis 42 is common to knobs 27 and 28 and to pinions 39 and 40 respectively integral with them. Upper reference mark holder 12s is thus displaceable, in the same way as lower reference mark holder 12i, through actuating control knob 28, vertically according to a path that is so slightly concave that it can be assimilated to a substantially rectilinear path situated substantially in the same vertical plane (perpendicular to optical axis 10) as the path of reference mark holder 12i.

The mixed lines indicate, in FIGS. 3 and 4, the high positions (12i" and 12s") and low positions (12i' and 12s') of respectively lower 12i and higher 12s reference mark holders.

Any classical mounting method for control knob 27 and 28 can be envisaged, which allows the optician to turn them independently from each other. In the example represented, knob 28 comprises a portion forming a pin or trunnion 47 and mounted in rotation in a bearing 48 provided in internal wall 30. Knob 27 is adapted to an axis 49 that is integral with it and rotatably mounted in a bore or boring 50 provided coaxially in knob 28 and its pin 47.

According to one preferred feature of the device according to the invention, the visual reading, by the optician, of the results of the pupillary spacing and height measurement is replaced or doubled by a digital display, obtained through means that will be described herein-below.

Figures 8, 9:
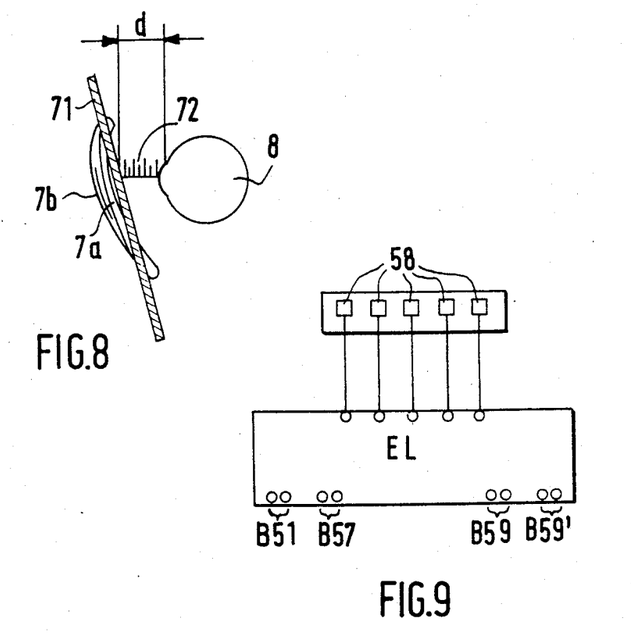
FIG. 9 is a greatly simplified diagram of the electronic equipment of the apparatus according to the invention.

Knob 28 bears, on its end forming trunnion or pin 47, the body 52 of a potentiometer 51. Resistance 53 of this potentiometer 51 is integral with body 52. Slider 54 of the potentiometer 51 is mounted on the free end of axis 49 of control knob 27 and electrically connected to a first terminal 55 of the potentiometer while one end of resistance 53 is connected to the second terminal 56 of the potentiometer. Terminals 55, 56 are suitably connected, in turn, (reference B51 in FIG. 9), to an electronic device EL that transforms in a manner known per se the output signals appearing at terminals 55, 56 of the potentiometer 51 into digital display signals visible in optical display windows 58, a plurality of which are provided on inclined wall 2 of housing 1, but only certain of them are schematically represented in FIGS. 2 and 9.

It will be understood that by virtue of the arrangement of potentiometer 51 in the form of a "differential" potentiometer, the optician, by adjusting by means of knob 27 reference mark 12a (FIG. 7) so that it is tangent to the lower edge of associated spectacle lens 7b, obtains a reference level for the output signal of the potentiometer, with respect to which the resulting signal, obtained and displayed after adjustment, by means of knob 28 in order to cause to pass reference mark 12b through the centre of the pupil of the eye involved, is representative of the distance between this lens edge and the pupil or, in other terms, representative of the "mounting height" of the lens concerned.

The description given above of the arrangement of the actuation means of reference mark holder 12 is equally applicable to the corresponding means associated to reference mark holder 11 that are symmetrically disposed with respect to the means mentioned above and function in the same way as them. In this way, control knob 25 is connected to the lower reference mark holder of pair 11 through a control mechanism 33 analogous to mechanism 35 described herein-above and hinged at 31 on internal wall 29 as described in particular with reference to FIGS. 3 and 4, while the upper reference mark holder of pair 11 is connected to knob 26 through a control mechanism 34 analogous to mechanism 36 associated to knob 27. Furthermore, knobs 25 and 26 are also associated to a potentiometer 57 similar to that described herein-above with reference to knobs 27, 28 and to potentiometer 51. The output terminals of potentiometer 57 are also connected to electronic device EL, as schematically indicated in B57 in FIG. 9, and one of windows 58 is intended to digitally display the equivalent of the output signal of potentiometer 57 thus applied to input B57 of electronic device EL.

Control knob 18 of space reference mark holder 13 is also associated to a potentiometer. This latter can be mounted with this purpose in such a way that its slider turns coaxially and integrally with knob 18, or indeed, as represented in FIG. 5, potentiometer 59 can comprise a coaxial pinion 61 meshing with rack 16a and connected to the slider of the potentiometer, the body of which is stationary with respect to housing 1.

Terminals 60 of the potentiometer are connected at B59 to the electronic device EL (FIG. 9).

In a similar way, the control knob of spacing reference mark holder 14 is connected to another potentiometer (not represented) the terminals of which are connected in B59' to the electronic device. This latter transforms the output signals of the two above-mentioned potentiometers into digital display signals. This displaying, by means of associated windows 58, can comprise a displaying of spacing $e_1$, a displaying of spacing $e_2$ (or "half spacing") as well as a displaying of the total of the two values $e_1 + e_2$, i.e. the total pupillary spacing.

The device according to the invention comprises, furthermore, two plane lateral mirrors 62 disposed on either side of target aperture 6 in vertical planes each inclined at an angle of 45° with respect to optical axis 10; this construction allows to respectively receive—through transparent walls 73 disposed in aperture 6—and return—, according to respective deflected optical paths 69 and 70, that cross through respectively recesses 29a and 30a provided for this purpose in internal walls 29 and 30, the respective images of the profile of the spectacle frame 7, and especially spectacle rims 7a and 7b of this frame. These images are received and returned by first reflecting mirrors 64, 65 in the direction of the optical axis 10 towards second reflecting mirrors 66, 7 which transmit them, preferably through a concave lens 68, towards target 4. Due to this fact, the optician perceives in his eye 5 the images of the profile superimposed on each eye 8 of the patient, of the spectacle rims 7a, of the spectacle lenses 7b and of the two inclined reference marks 71 disposed respectively on lateral mirrors 62 and 63, as will be seen from FIG. 8. The image of the two horizontal graduated scales 72 also provided on the two lateral mirrors respectively, being perceived at the same time by the optician, he can appreciate the distance between each pupil of the patient and the associated spectacle lens 7b.

It therefore becomes apparent from the above description, that in order to determine the parameters concerned by the mounting of spectacle lenses on a frame, the optician places the device before the patient wearing the spectacles, in such a way that the spectacles and the patient's eyes are in the target aperture 6, the median nasal plane 22 of the patient being perpendicular to optical axis 10 and situated at least substantially at the centre between two lateral ends of target aperture 6. Suitable nasal, facial and/or chin rests can be provided on the device in order to facilitate its positioning and its maintenance in position with respect to the patient during the measuring operations. The optician thus reads off the distance between the eye of the patient and the associated lens, as indicated in FIG. 8, and by acting, as described herein-above on control knobs 18, 19, 25, 26, 27 and 28 he adjusts the different reference mark lines for measuring the spacing and the height in order to read off either by direct reading by means of graduated scales, or by observing digital display windows 58, the half spacings and pupillary spacings, as well as the height of the mounting, in a simple and single operation which, is not tedious.

Figure 11:
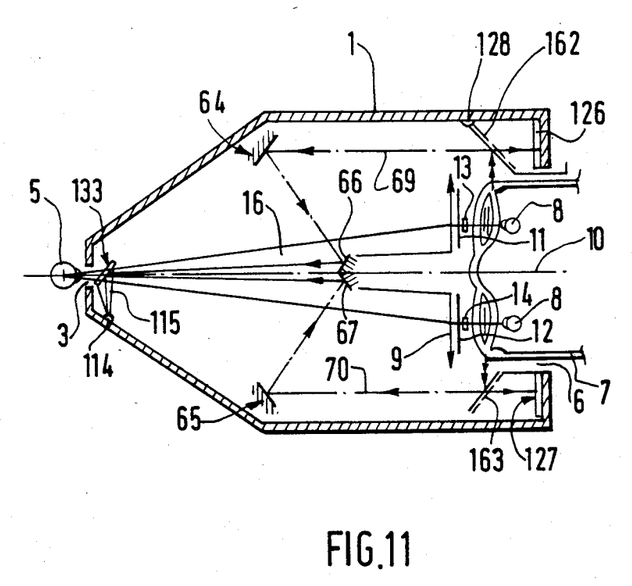
FIG. 11 represents another embodiment of the device according to FIG. 1.

FIG. 11 shows another embodiment that corresponds basically to that which has been described herein-above with reference to the preceding drawings. The following description will thus be substantially limited to the characteristics by which the device according to FIG. 11 is distinguished from the device according to FIGS. 1 to 10. It should be noted that to the extent that the constitutive elements of the device of FIG. 11 are similar to those of the device according to the preceding embodiment, they are designated by the same numerical references as those used for FIGS. 1 to 10.

According to FIG. 11, lateral mirrors 62, 63 of the embodiment according to FIG. 1 comprised semi-transparent mirrors 162, 163 that are optically associated to plates 126, 127 disposed to the rear of the above-mentioned semi-transparent mirrors. Plates 126, 127 present graduated distance scales 78 (cf. FIG. 8) while semi-transparent mirrors 162, 163 bear distance reference mark lines 71 (FIG. 8). These reference mark lines being inclined, and at least one of the semi-transparent mirrors—for example, mirror 162—being pivotally mounted around an axis 128 orthogonal to optical axis 10, it is sufficient to cause to pivot the concerned lateral mirror in an appropriate way in order to cause reference mark 71 to coincide substantially with the profile of associated spectacle rim 7a to have throughout the width of the pivoting movement, an inclination measurement of the said spectacle rim with respect to a reference vertical.

Furthermore, according to FIG. 11, light source 114 is shifted with respect to the optical axis, adjacent to the eye-piece of the device, and another appropriately inclined semi-transparent mirror 133 receives rays 115 from this source in order to transmit them towards target aperture 6, while allowing to pass towards eye-piece aperture 3 the deflected rays, as described hereinabove.

Handling of the device represented in FIG. 11 is substantially similar to that which was described in reference to the preceding embodiment.

In every embodiment of the present invention, the reference marks, either in the forms of lines, cross hair-lines or otherwise, can be formed through using liquid crystals the displacement of which is controlled by electric and electronic means associated to the device.

It will becomes apparent from the preceding description that the device according to the invention can be very simply constructed, only comprising a minimum of optical components. It is also relatively inexpensive, among other reasons due to the fact that it can, wherever necessary, be utilized without the need of any semi-transparent mirror.

Furthermore, the optical paths defined by the device being relatively close in space, the accommodation obligation, by the optician, is reduced to a minimum, if not suppressed completely.

The present invention is not limited to the embodiment described and represented; it is adaptable to numerous modifications and variants available to the man skilled in the art, without departing from the spirit of the invention such as defined in the annexed claims.

I claim:

1. Device for measuring the ocular parameters of a patient, especially parameters for mounting ophthalmic lenses on a spectacle frame with a view to their adaptation to the patient, comprising a housing defining on one of its ends, a target aperture intended to receive the spectacle rims and lenses worn by the patient and, at the opposite end, an ocular aperture aligned on the said target aperture and provided with an eye-piece adapted to be observed by the operator, the said housing containing a light source adapted to emit a luminous beam towards the said target aperture, a bi-convex lens interposed between the said target opening and the said eye-piece so that its optical axis coincides with that of the eye-piece and the said lens forms for the operator, in association with the eye-piece, frontal images of lenses and spectacle rims and of the eyes of the patient, reference mark means that are intended to be adjusted with respect to the eyes of the patient and the image of which is intended to be observed, through the said eye-piece, simultaneously with the said frontal image, wherein the said reference mark means comprise two spacing reference marks, each disposed on a transparent portion of a spacing reference mark holder, displaceable independently from each other horizontally and perpendicularly to the optical axis mentioned above, by a control mechanism manually actuated by using a spacing adjustment member, accessible from outside the housing, the said reference mark means furthermore comprising two pairs of height reference marks respectively associated to the two eyes of the patient, each height reference mark being disposed on a transparent portion of a height reference mark holder vertically displaceable independently from the other, the said reference mark means comprising furthermore two distance reference marks each associated to a lateral mirror laterally placed with respect to one of the patient's eyes, in a vertical plane inclined at 45° with respect to the optical axis so as to receive the image of the profile of this eye, of the associated ophthalmic lens and of the spectacle rim and to transmit it to a first deflecting mirror placed in a vertical plane perpendicular to that of the said lateral mirror and transmitting the above-mentioned profile image towards the optical axis towards a second deflecting mirror placed adjacent to the said axis in a vertical plane inclined at 45° with respect to that of the said first deflecting mirror so as to transmit the said profile image towards the eye-piece and wherein the said device comprises measuring means to evaluate the position of the different above-mentioned reference marks with respect to the patients eyes, to the said ophthalmic lenses and to the said frame, and to visualize the results of this evaluation.

2. Device according to claim 1, wherein the control mechanism of each of said two spacing reference mark holders comprises a rectilinear rack extending transversally to the optical axis and meshing with a pinion integral with a spacing adjustment knob and coaxial to it, the said knob being rotatably mounted around a vertical axis orthogonal to the optical axis, and extending from the wall of the housing which is opposite the target aperture, the said rack being integral with one of the ends of a rod that bears at its other end the spacing reference mark concerned.

3. Device according to claim 1, wherein the control mechanism of each of the two reference mark holders of each pair of height reference mark holders comprises a control rod, mounted by hinged means at a position situated between its two ends, on a vertical and horizontal internal wall, of the housing, in a displaceable manner in a vertical plane parallel to the above-mentioned optical axis and bearing at one of its ends the respective height reference mark holder, while the said hinged means comprise a guiding pin laterally disposed on the control rod and slidingly engaged in a curved guiding groove provided in the said internal wall, and a curved rack meshing with a pinion integral with a height adjustment knob and coaxial to it, the arrangement being such that each reference mark holder is displaced, upon actuation of the associated adjustment knob, according to a substantially rectilinear vertical path.

4. Device according to claim 1, wherein the two spacing reference marks are associated to a graduated spacing scale allowing to measure the horizontal distance between these reference marks and the horizontal distance between the vertical median nasal plane of the patient and each of the said spacing reference marks, the said spacing scale being disposed on a fixed transparent plaquette mounted in the housing between the target aperture and the spacing and height reference mark holders, wherein each pair of reference mark holders is associated to a height graduated scale allowing to measure the vertical distance between the two respective reference marks of each pair of height reference mark holders, the said height scale being disposed on a portion of the lower reference mark holder of each pair that covers at least partially the associated upper reference mark holder, and wherein the distance reference marks are each associated to a graduated distance scale disposed on the lateral mirror involved, and allowing to measure, in the image received by the target, the distance between the cornea of the patient and the associated distance reference mark.

5. Device according to claim 1, wherein the control mechanisms of the spacing reference mark holders and the height reference mark holders are associated to electric and electronic means intended to detect the distances between the associated reference marks, to produce electric signals representative of these distances, to transform these electric signals into digital signals and to utilize them for visually displaying in digital form the said distances by means of display windows disposed on one of the walls of the housing.

6. Device according to claim 5, wherein the two control knobs for adjusting the control mechanism of each pair of height reference mark holders are connected respectively to the slider and to the resistance of a rotary potentiometer the terminals of which are connected to at least one input terminal of the said electronic means of which at least one output terminal is connected to one of the above-mentioned windows that digitally display the value of the effective resistance of the potentiometer determined by the relative angular position of the two above-mentioned knobs and representing the vertical distance between the two height reference marks involved.

7. Device according to claim 6, wherein each control knob is connected to the slider of a potentiometer the terminals of which are connected to input terminals, of the said electronic means of which at least one output terminal is connected to at least one of the said windows which digitally displays the value of the effective resistance of the potentiometer determined by the angular position of the adjustment knob involved.

8. Device according to claim 1, wherein the said light source is an annular light source coaxially juxtaposed at the said eye-piece so that it is not directly visible to the operator's eye.

9. Device according to claim 1, wherein the said light source is constituted by four punctual diodes disposed at the four corners of a square so that they are not directly visible to the operator's eye, the centre of the square being on the optical axis of the eye-piece.

10. Device according to claim 1, wherein the above-mentioned lateral mirrors are semi-transparent mirrors that are each provided with an adjustment mark and behind each of which is disposed a plate provided with a distance scale, so that the said eye-piece receives, for each of the patient's eyes, simultaneously the profile image of the eye, the profile image of a respective eye-wire or rim, the image of the reference mark line and the image of the said distance scale.

11. Device according to claim 10, wherein at least one of the semi-transparent lateral mirrors is advantageously mounted pivotally around an axis that is orthogonal to the said optical axis, so that in the image received in the eye-piece the suitably oriented reference mark of this semi-transparent lateral mirror can be brought through pivoting to be substantially superimposed upon the profile of the spectacle rim or eye wire, while the angle of this pivoting represents the inclination of the said rim.

12. Device according to claim 10, wherein the light source is shifted with respect to the said optical axis and the light beam is sent towards the target aperture through a semi-transparent mirror inclined with respect to this axis and interposed on it between the said target aperture and the said eye-piece, towards which it allows to pass the reflected images of the spectacles and the eyes of the patient, as well as the images of the respective reference means.

* * * * *